US00PP30914P3

(12) United States Plant Patent
Sakurai

(10) Patent No.: US PP30,914 P3
(45) Date of Patent: Oct. 1, 2019

(54) ***VACCINIUM* PLANT NAMED 'RYOKU NH-13'**

(50) Latin Name: ***Vaccinium corymbosum* L.**
Varietal Denomination: RYOKU NH-13

(71) Applicant: NIPPON RYOKUSAN CO., LTD., Matsumoto-shi (JP)

(72) Inventor: Shigetaka Sakurai, Matsumoto (JP)

(73) Assignee: NIPPON RYOKUSAN CO., LTD., Matsumoto-shi (JP)

( * ) Notice: Subject to any disclaimer, the term of this patent is extended or adjusted under 35 U.S.C. 154(b) by 0 days.

(21) Appl. No.: 15/732,726

(22) Filed: Dec. 21, 2017

(65) Prior Publication Data

US 2018/0192559 P1 Jul. 5, 2018

(30) Foreign Application Priority Data

Jan. 4, 2017 (JP) ..... 31725

(51) Int. Cl.
*A01H 5/08* (2018.01)
*A01H 6/36* (2018.01)

(52) U.S. Cl.
USPC ..... Plt./157
CPC ..... *A01H 5/08* (2013.01)

(58) Field of Classification Search
USPC ..... Plt./157
CPC . A01H 5/08; A01H 5/00; A01H 6/368; A01H 5/02; A01H 6/36
See application file for complete search history.

*Primary Examiner* — June Hwu
(74) *Attorney, Agent, or Firm* — Oblon, McClelland, Maier & Neustadt, L.L.P.

(57) ABSTRACT

A new and distinct variety of *Vaccinium corymbosum* L. plant named 'RYOKU NH-13', characterized by having a more upright plant growth habit, stronger plant vigor, comparatively early fruit ripening time, comparatively large fruit size, sweeter fruits, better taste balance of sweetness and acidity, and smaller stem scar.

8 Drawing Sheets

The latin name of the genus and species of the novel variety disclosed herein is: *Vaccinium corymbosum* L.

The novel variety of the *Vaccinium corymbosum* L. disclosed herein has been given the variety denomination: 'RYOKU NH-13'.

CROSS-REFERENCE TO RELATED APPLICATIONS

This application claims the benefit of Japanese Plant Breeders' Rights Application No. 31725, filed Jan. 4, 2017, which is incorporated by reference herein as if set forth in its entirety.

BACKGROUND OF THE INVENTION

The present invention relates to a new and distinct hybrid variety of northern highbush blueberry (*Vaccinium corymbosum* L.) named 'RYOKU NH-13'. This novel variety was found by open pollination of 'Chandler', a seed parent variety, in the tests conducted for the period from 2003 to 2007 in Matsumoto-City, Nagano-prefecture, Japan. As stated below, 'RYOKU NH-13' has apparently different characteristics from those of the varieties 'Chandler' and 'Blueray', both being widely planted and being important varieties in the Chubu district of Japan.

SUMMARY OF THE INVENTION

Blueberry variety 'RYOKU NH-13' exhibits outstanding and distinguishing characteristics when grown under normal horticultural conditions in the area from Nagano-prefecture to the north of the Kanto in Japan, including:

(1) more upright plant growth habit and stronger plant vigor;
(2) comparatively early fruit ripening time (on average, around July 10 of each year in Matsumoto, Nagano, Japan);
(3) comparatively large fruit size;
(4) sweeter fruits;
(5) better taste balance of sweetness and acidity;
(6) smaller stem scar.

BRIEF DESCRIPTION OF THE DRAWINGS

The accompanying colored photographs (FIGS. 1-8) show typical bush, flower, fruit and leaf characteristics for the new *Vaccinium corymbosum* L. plant, 'RYOKU NH-13'. Colors shown are as accurate as can be reasonably reproduced by photographic means. In some cases, the color might differ slightly from the colors of 'RYOKU NH-13' recited in the description.

DETAILED BOTANICAL DESCRIPTION

A. Distinctive Characteristics of 'RYOKU NY-11'

Figure 1:
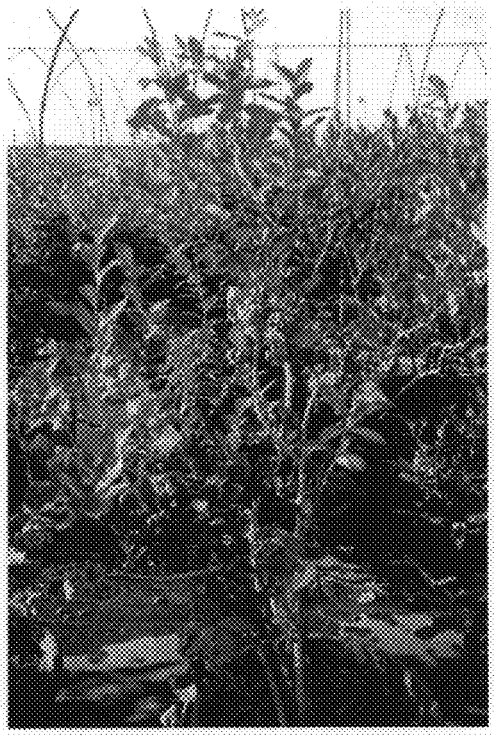
FIG. 1 shows a tree body of 'RYOKU NH-13' (photographed date: Jul. 10, 2015; photographed location: Matsumoto-City, Nagano-prefecture, Japan; and the age of photographed 'RYOKU NH-13': 5 years).
Figure 2:
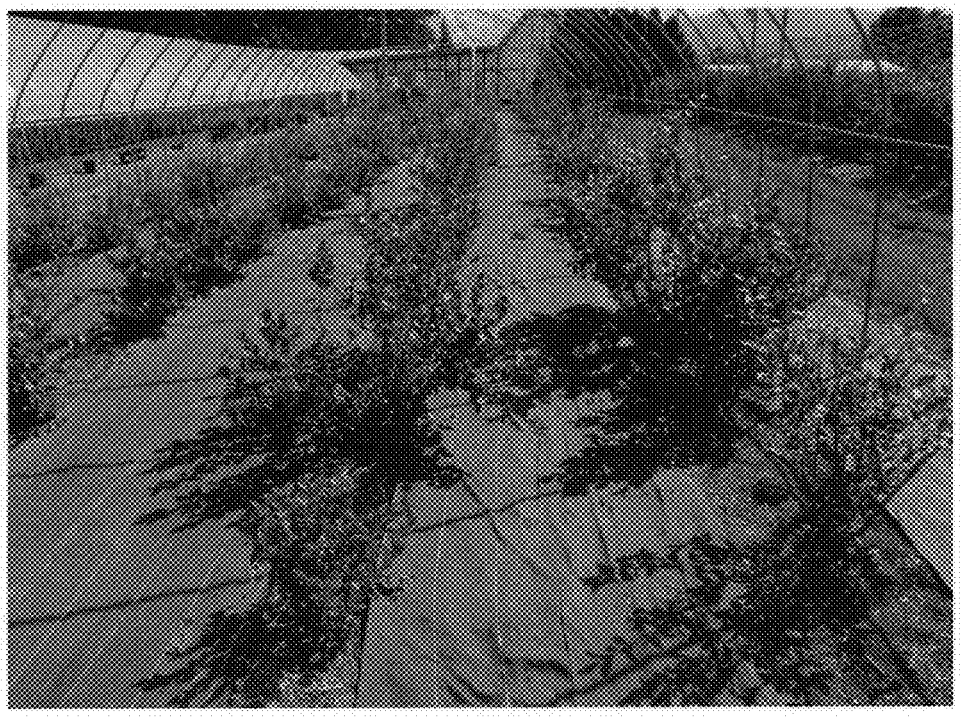
FIG. 2 shows a panoramic view of the cultivation area of 'RYOKU NH-13' (photographed date: Sep. 7, 2012; photographed location: same as FIG. 1; and the age of photographed 'RYOKU NH-13': 5 years).
Figure 3:
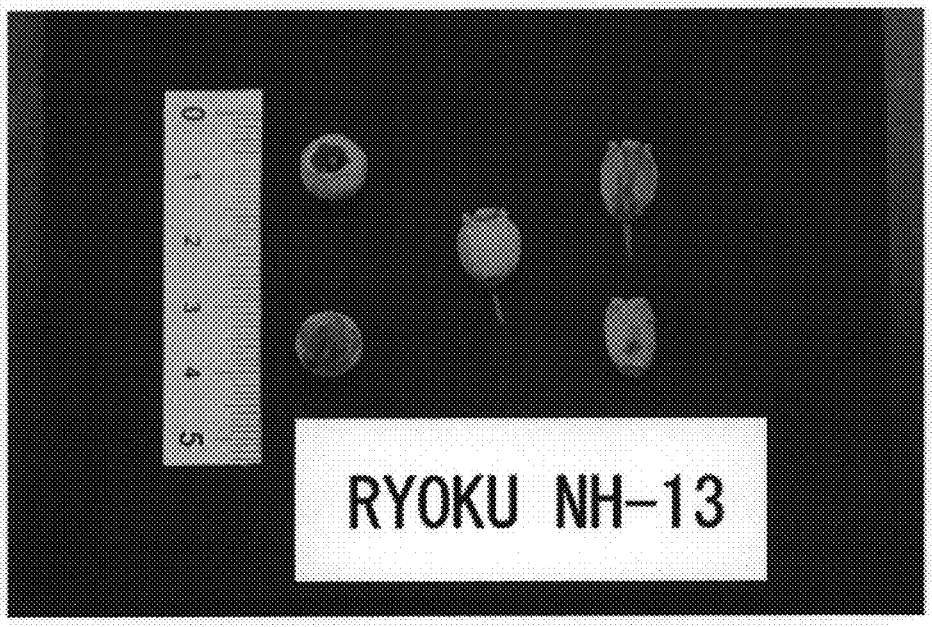
FIG. 3 shows whole flowers of 'RYOKU NH-13' (photographed date: May 8, 2015; photographed location: same as FIG. 1; and the age of photographed 'RYOKU NH-13': 5 years).
Figure 4:
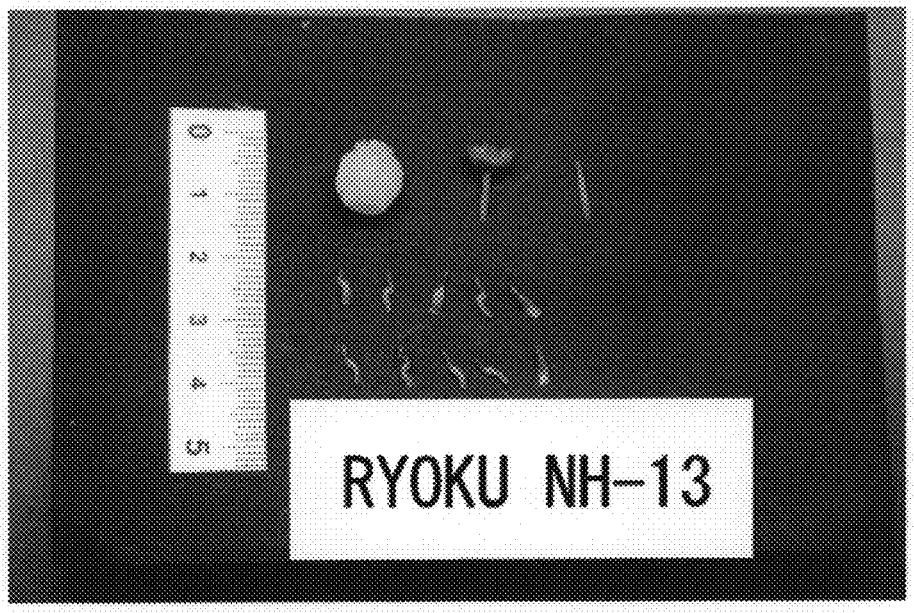
FIG. 4 shows broken-down parts of the flower of 'RYOKU NH-13' (photographed date: May 8, 2015; photographed location: same as FIG. 1; and the age of photographed 'RYOKU NH-13': 5 years).
Figure 5:
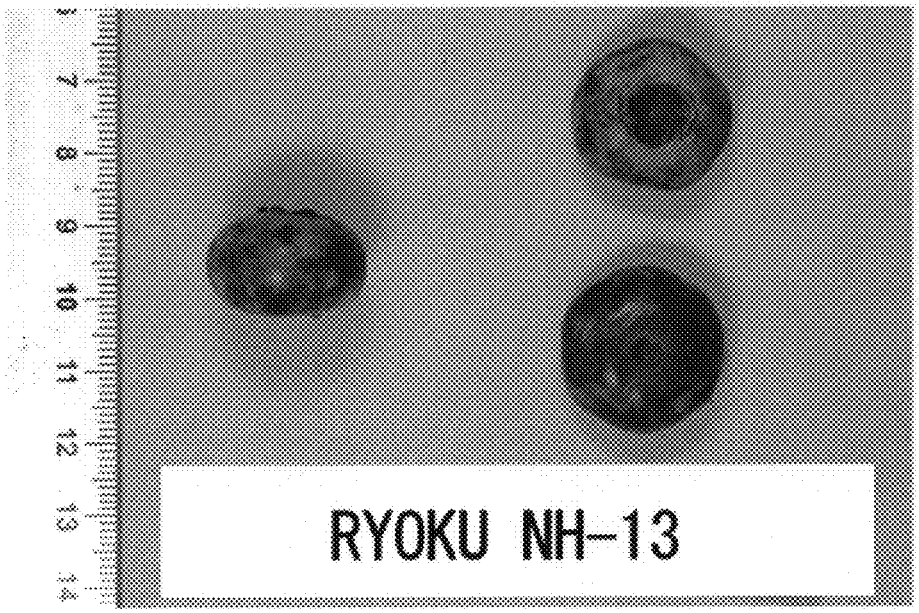
FIG. 5 shows fruits of 'RYOKU NH-13' (photographed date: Jul. 14, 2014; photographed location: same as FIG. 1; and the age of photographed 'RYOKU NH-13': 5 years).
Figure 6:
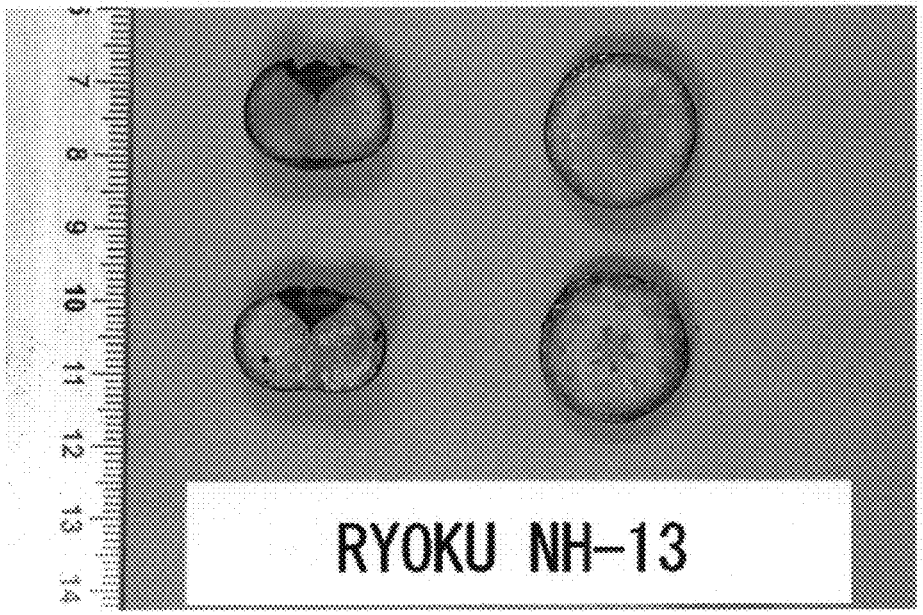
FIG. 6 shows a cross-section of the fruits of 'RYOKU NH-13' (photographed date: Jul. 14, 2014; photographed location: same as FIG. 1; and the age of photographed 'RYOKU NH-13': 5 years).
Figure 7:
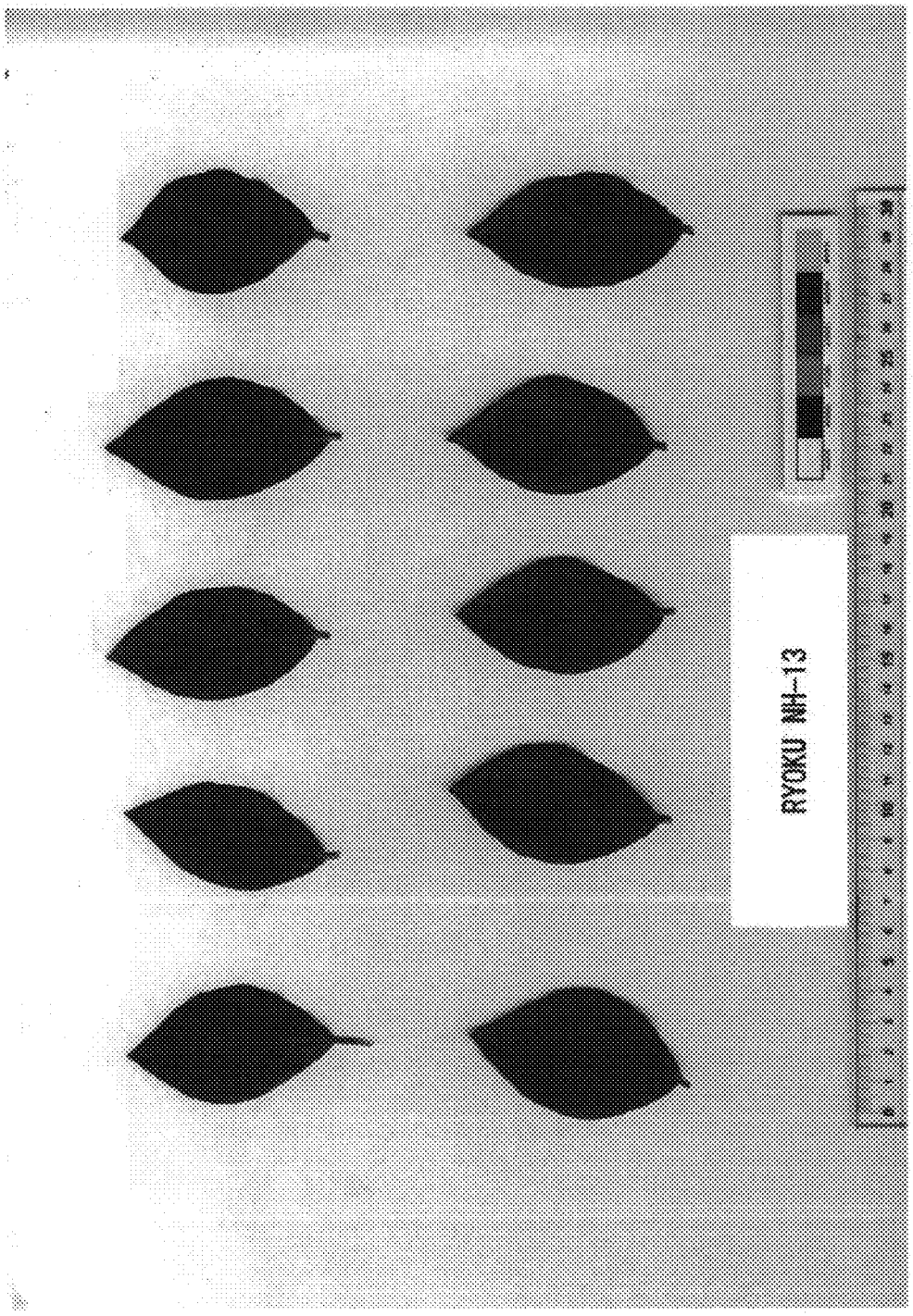
FIG. 7 shows an upper side of the leaves (10 sheets) of 'RYOKU NH-13' (photographed date: Jul. 22, 2014; photographed location: same as FIG. 1; and the age of photographed 'RYOKU NH-13': 5 years).
Figure 8:
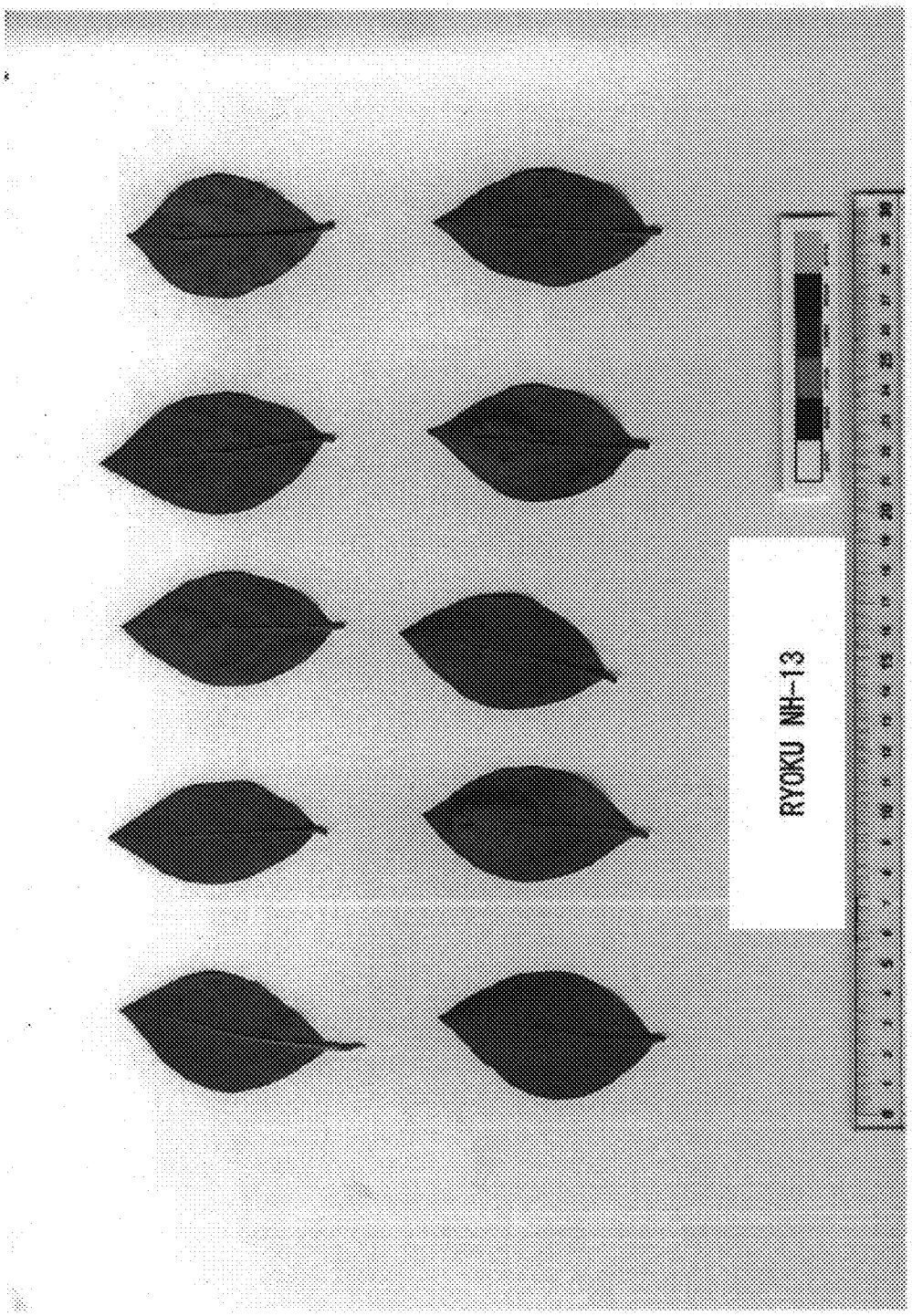
FIG. 8 shows a lower side of the leaves (10 sheets) of 'RYOKU NH-13' (photographed date: Jul. 22, 2014; photographed location: same as FIG. 1; and the age of photographed 'RYOKU NH-13': 5 years).

As described above, 'RYOKU NH-13' was obtained by the open pollination of 'Chandler', a seed parent (Note: the possible pollen parent might be 'Blueray'). On Apr. 15, 2003, about 10,000 seeds of 'Chandler', which were cultivated in a field in Matsumoto-City, Nagano-prefecture, Japan, were seeded in plant seeding trays, and then transplanted to pots. The resulting seedlings (about 3,000) were planted in cultivation pots on May 1, 2004. Fructification of the planted seedlings were started from Jun. 20, 2007 (on Year 3), and about 200 plant individuals were selected based on the characteristics, including larger fruit size, better taste balance of sweetness and acidity, higher yield per plant, earlier ripening time, large and uniform fruits, etc.. For the about 200 selected plant individuals, test plots (each including about 20 cuttings per plant individual) were formed, where these plants were asexually propagated by cutting means. During the period from Jul. 20, 2009 to Dec. 25, 2016 and for 3 generations, the plants were propagated and examined for their characteristics based on the growth, yield and fruits quality in each test plot. For 10 test plots, the characteristics of the plants were observed for the period between the flowering time and the ripening time yearly for 5 years, and since neither variant nor off-type plant was observed for the period, the characterization of 'RYOKU NH-13' was finished on Dec. 25, 2016 and the breeding was completed.

'RYOKU NH-13' is a blueberry clone which can be distinguished from the important blueberry varieties 'Chandler' and 'Blueray', both of which are widely planted in the Chubu district of Japan, due to its characteristics including a more upright plant growth habit, stronger plant vigor, comparatively early fruit ripening time, comparatively large fruit size, sweeter fruits, better taste balance of sweetness and acidity, and smaller stem scar. From the above-described about 200 selected plant individuals, one plant individual, 'RYOKU NH-13', was selected out as described, and then 31 plants were propagated from 'RYOKU NH-13' by cutting means in Matsumoto, Nagano, Japan, and all the resulting plants were phenotypically indistinguishable from the original plant variety 'RYOKU NH-13'. In addition, comparing to 'Chandler' and 'Blueray', the claimed plant 'RYOKU NH-13' has a more upright plant growth habit, about 1 week to 10 days earlier fruit ripening time (on average, around July 10 of each year in Matsumoto, Nagano, Japan), sweeter fruits, and smaller stem scar when compared to its related variety 'Chandler', and has stronger plant vigor, larger fruit size, better taste balance of sweetness and acidity, and smaller stem scar when compared to 'Blueray' (see Table 1 below). It should be noted that the plant age of all the plants of 'RYOKU NH-13', which were observed for botanical description, was 5 years.

The following data defining the characteristics of 'RYOKU NH-13' were collected from the asexual propagation by cutting means carried out in Matsumoto, Nagano, Japan. The plant history was taken on a plot of 10 five-year-old plants growing in Matsumoto, Nagano, Japan. 'RYOKU NH-13' has not been observed under all possible environmental conditions, and the measurements provide might therefore vary when grown in different environments. Where averages are given, the sample size was 10.

B. Phenotypic Description of *Vaccinium corymbosum* L. ('RYOKU NH-13')

Characteristics of 'RYOKU NH-13' are further specifically described as follows:

1. Plant:
   - *Plant vigor.*—Strong, where the plant vigor is stronger than 'Blueray'.
   - *Plant size.*—Large.
   - *Growth habit.*—Upright.
   - *Plant height.*—1.8 m on average for 5-year old plant.
   - *Plant spread.*—1.1 m on average for 5-year old plant.
   - *Color of bark of plant.*—Dark Red, 187-A (The R.H.S. Colour Chart).
   - *Tendency toward evergreen.*—Absent.
   - *Cold hardiness.*—Survived in winter frost (below −10° C.) with minimum damage.
   - *Ease of propagation.*—Propagated by each of dormant wood cutting and softwood stem cutting, where the rooting percentage was greater than 70% and comparable to the other varieties.
2. Trunk and branches:
   - *Suckering tendency.*—Less sucker as in 'Chandler'.
   - *Surface texture (of 6-month-old shoots).*—Lustrous.
   - *Surface texture (of 3-year-old and older wood).*—Lustrous.
   - *Color of new twigs observed in the field.*—Orangish yellow green.
   - *Internode length.*—20.4 mm on average.
3. Leaves:
   - *Leaf length including petiole.*—70.4 mm on average.
   - *Leaf width of leaf at widest point.*—39.2 mm on average.
   - *Leaf shape.*—Elliptic.
   - *Leaf margin.*—Entire.
   - *Color.*—Upper surface of leaves: Dark Green, 136-A. Lower surface of leaves: Deep Yellowish Green, 141-B (The R.H.S. Colour Chart).
   - *Pubescence.*—Upper Surface of leaves: Absent. Lower Surface of leaves: Absent. Margins: Absent.
   - *Timing of vegetative bud burst.*—Medium.
4. Flowers:
   - *Shape.*—Campanulate.
   - *Color of opened flower.*—Pale Yellow Green, 157-C (The R.H.S. Colour Chart).
   - *Color of sepal.*—Light Yellowish Green, 135-D (The R.H.S. Colour Chart).

*Flowering period.*—Mean date of 50% opening of flowers in Matsumoto-City, Nagano-prefecture, Japan is May 3, equivalent to 'Chandler'.

*Corolla.*—Diameter: 9.4 mm on average. Length (from pedicel attachment point to corolla tip excluding the pedicel): 12.0 mm on average. Color: White. Anthocyanin coloration in corolla tube — Medium.

5. Reproductive organs:

*Pollen.*—Color: Yellow.

6. Fruit:

*Mean date of 50% harvest in Matsumoto-City, Nagano-prefecture.*—July 10.

*Diameter of calyx aperture on mature berry.*—7.6 mm on average.

*Size and shape of calyx lobe on mature berry.*—Medium size, outcurving, and having deep calyx basin.

*Detachment force for ripe berries (easy, medium, hard).*—Easy.

*Fruit cluster density (sparse, medium, dense).*—Medium to slightly dense.

*Fruiting type.*—On one-year old shoots only.

7. Berry:

*Cluster (tight, medium, loose).*—Medium.

*Weight (on well-pruned plants).*—3.81 g on average.

*Height.*—13.3 mm on average.

*Width.*—21.3 mm on average.

*Shape.*—Oblate.

*Surface color of mature berries ripe on the plant.*—Light Purplish Blue, 98-D (The R.H.S. Colour Chart).

*Intensity of fruit bloom.*—Medium.

*Surface color of ripe berry after polishing.*—Greyish Purplish Blue, 103-A (The R.H.S. Colour Chart).

*Immature berry color, with bloom.*—Light Yellowish Green, 140-D (The R.H.S. Colour Chart).

*Immature berry color, without bloom.*—Brilliant Yellow Green, 149-A (The R.H.S. Colour Chart).

*Flesh color.*—Pale Yellow Green, 149-D (The R.H.S. Colour Chart).

*Peel color.*—Medium blue.

*Color of seeds.*—Moderate Yellow, 162-A (The R.H.S. Colour Chart).

*Pedicel scar.*—Medium, 2.54 mm on average.

*Firmness.*—Medium.

*Intensity of fruit sweetness.*—High, Bx 12.3.

*Intensity of fruit acidity.*—High, pH 2.55.

*Texture.*—Crispy, juicy, medium seeds.

8. Use: 'RYOKU NH-13' produce northern highbush blueberries suitable for fruit-picking farms, fresh fruit markets and processed fruit markets, etc.

9. Resistance to disease, insects, and mites: 'RYOKU NH-13' grew vigorously and showed excellent bush survival in the field. It appears to be tolerant to stem blight (*Botryosphaeria* spp.) and root rot (*Phytophthora cinnamoni*), with very few young plants dying soon after planting. The response of 'RYOKU NH-13' to the various fungal species that cause summer leaf spots is typical of other northern highbush varieties, and fungicide applications may be needed after harvest in order to reduce foliar diseases and to retain leaves until autumn and make maximum flower bud set. Similarly, susceptibility to typical blueberry insect and mite pathogens, such as spotted wing drosophila (*Drosophila suzukii*), blueberry gall midge (*Dasineura oxycoccana*) and blueberry bud mite (*Acalitus vaccini*) is similar to other northern highbush cultivars.

TABLE 1

(Comparison of characteristics among varieties)

| Charact. No | UPOV No. | Code | Characteristics | Definition |
|---|---|---|---|---|
| 1 | 1 (*) | QN (+) | Plant: vigor | Strength of growth level of plant |
| 2 | | QN | Plant: size | Size of plant crown |
| 3 | 2 (*) | QN G | Plant: growth habit | Whole shape of plant without pruning during dormant period |
| 4 | 3 | PQ | One-year-old shoot: color | Color of middle part of shoot extended before dormant period |
| 5 | | QN | One-year-old shoot: length | Length of middle part of shoot extended before dormant period |
| 6 | 4 | QN | One-year-old shoot: length of internode (upper half) | Length of internode of shoot extended before dormant period (upper half) |
| 7 | 5 (*) | QN | Leaf: length | Length of leaf sufficiently expanded |
| 8 | 6 | QN | Leaf: width | Maximum width of mature leaf |
| 9 | 7 | QN | Leaf: ratio length/width | Ratio of leaf length to maximum width (leaf length/leaf width) |
| 10 | 8 (*) | PQ | Leaf: shape | Shape of mature leaf |
| 11 | | QN (+) | Leaf: shape of tip | Shape of lip of mature leaf |
| 12 | 9 | QL | Leaf: color of upper side | Color of surface of mature leaf |
| 13 | 10 (*) | QN | Only varieties with green leaf color: Leaf, intensity of green color on upper side | Intensity of green color on surface of mature leaf |
| 14 | 11 (*) | QL | Leaf: margin | Type of margin of mature leaf |
| 15 | 12 | QN | Flower bud: anthocyanin coloration | Intensity of anthocyanin coloration of flower bud occurring to one year old shoot |
| 16 | 13 | QN | Inflorescence: length (excluding peduncle) | Length of inflorescence at flowering time (excluding peduncle) |
| 17 | 14 | PQ | Flower: shape of corolla | Shape of corolla at full bloom |
| 18 | | PQ | Flower: color of corolla | Color of corolla at full bloom |
| 19 | 15 (*) | QN | Flower: size of corolla tube | Size of corolla tube at full bloom |
| 20 | 16 (*) | QN | Flower: anthocyanin coloration of corolla tube | Intensity of anthocyanin coloration on surface of corolla tube |
| 21 | 17 | QL | Flower: ridges on corolla tube | Presence or absence of ridges on corolla tube |
| 22 | 18 | QN | Fruit cluster: density | Density of fruit per fruit cluster |

TABLE 1-continued (Comparison of characteristics among varieties)

| | | | | |
|---|---|---|---|---|
| 23 | 19 (*) | QN | Unripe fruit: intensity of green color | Intensity of green color of fruit before ripening |
| 24 | 20 (*) | QN | Fruit: size | Size of fruit at ripening |
| 25 | 21 (*) | PQ (+) | Fruit: shape in longitudinal section | Shape in longitudinal section of fruit at ripening |
| 26 | | QN (+) | Fruit: size of scar | Size of stem scar of mature fruit |
| 27 | | PQ (+) | Fruit: shape of calyx cavity | Shape of calyx cavity of mature fruit |
| 28 | 22 | QN | Fruit: attitude of sepals | Attitude of sepals relative to mature fruit |
| 29 | 23 | QN | Fruit: type of sepals | Direction of curving of sepals |
| 30 | 24 | QN | Fruit: diameter of calyx basin | Diameter of calyx basin of mature fruit |
| 31 | 25 | QN | Fruit: depth of calyx basin | Depth of calyx basin of mature fruit |
| 32 | 26 (*) | QN | Fruit: intensity of bloom | Intensity of bloom on surface of mature fruit |
| 33 | 27 (*) | PQ G | Fruit: color of skin (after removal of bloom) | Color of skin of mature fruit after removal of bloom |
| 34 | 28 | QN (+) | Fruit: firmness | Firmness of mature fruit |
| 35 | | PQ | Fruit: color of flesh | Color of flesh of mature fruit |
| 36 | 29 (*) | QN (+) | Fruit: sweetness | Sweetness of mature fruit |
| 37 | 30 (*) | QN (+) | Fruit: acidity | Acidity of mature fruit |
| 38 | 31 (*) | QL G | Plant: fruiting type | Shoots to which fruits adnate |
| 39 | | QN | Fruit: tendency of cracking | Tendency of cracking during harvest season |
| 40 | 32 (*) | QN (+) | Time of vegetative bud burst | Time of beginning to burst first vegetative bud of each individual plant |
| 41 | 33 (*) | QN (+) G | Time of beginning of flowering on one-year-old shoot | Time of 10% flowering occurring to one year old shoot |
| 42 | 34 (*) | QN (+) G | Varieties which fruit on one-year-old shoot and current season's shoot: Time of beginning of flowering on current year's shoot | Time of 10% flowering occurring to current year's shoot |
| 43 | 35 | QN (+) G | Time of beginning of fruit ripening on one-year-old shoot | Time of 10% fruit ripening on one year old shoot |
| 44 | | QN | Period of harvest | Length of harvest period of fruit |
| 45 | 36 (*) | QN (+) G | Varieties which fruit on one-year-old shoot and current season's shoot: Time of beginning of ripening on current year's shoot | Tme of 10% fruit ripening on current year's shoot |

TABLE 1-continued (Comparison of characteristics among varieties)

| Charact. No | Method | Class | State | Standard Variety (E.x. Var.) |
|---|---|---|---|---|
| 1 | Observation (a) VG | 3 | weak | Bluetta, Meader |
| | | 5 | medium | Collins, Weymouth |
| | | 7 | strong | Berkeley, Homebell, Woodard |
| 2 | Observation (a) VG | 3 | small | Avonblue, Bluetta, Flordablue |
| | | 5 | medium | Bluecrop, Earliblue |
| | | 7 | large | Dixi, Homebell, Tifblue |
| 3 | Observation (a) VG | 1 | upright | Becyblue, Bluechip, June, Spartan |
| | | 2 | semi-upright | Bluecrop, Lateblue |
| | | 3 | spreading | Northland, Weymouth |
| 4 | Observation (a) VG | 1 | green | |
| | | 2 | greenish red | |
| | | 3 | greyish red | Briteblue, Homebell |
| | | 4 | reddish yellow | Berkeley, Dixi |
| | | 5 | reddish brown | Blueray, Darrow, Weymouth |
| | | 6 | dark red | |
| 5 | Measurement mm (a) VG | 3 | short | |
| | | 5 | medium | |
| | | 7 | long | |
| 6 | Observation (a) VG | 3 | short | Avonblue, Weymouth |
| | | 5 | medium | |
| | | 7 | long | Jersey |
| 7 | Measurement mm (b) MS/VG | 3 | short | |
| | | 5 | medium | |
| | | 7 | long | |
| 8 | Measurement mm (b) MS/VG | 3 | narrow | |
| | | 5 | medium | |
| | | 7 | broad | |
| 9 | Measurement (b) MS/VG | 3 | small | |
| | | 5 | medium | |
| | | 7 | large | |
| 10 | Observation (b) VG | 1 | lanceolate | |
| | | 2 | ovate | Northland |
| | | 3 | elliptic | Berkeley, Collins, Coville |
| | | 4 | oblong | |
| 11 | Observation (b) VG | 3 | acute | Weymouth, Woodard |
| | | 5 | slightly acute | Earliblue, Tifblue |
| | | 7 | obtuse | Berkeley, Climax, Southland |
| 12 | Observation (b) VG | 1 | yellow | |
| | | 2 | green | Bluechip, Bluecrop, Blueray |
| 13 | Observation (b) VG | 3 | light | |
| | | 5 | medium | |
| | | 7 | dark | |
| 14 | Observation (b) VG | 1 | entire | |
| | | 2 | serrate | |

TABLE 1-continued (Comparison of characteristics among varieties)

| | | | | |
|---|---|---|---|---|
| 15 | Observation (a) VG | 3 | weak | |
| | | 5 | medium | |
| | | 7 | strong | |
| 16 | Measurement mm (c) MS/VG | 3 | short | |
| | | 5 | medium | |
| | | 7 | long | |
| 17 | Observation (c) VG | 1 | urceolate | Bluecrop, Jersey |
| | | 2 | campanulate | Northblue, Northsky |
| | | 3 | cylindrical | |
| 18 | Observation (c) VG | 1 | white | Aliceblue, Bluetta, Briteblue |
| | | 2 | creamy white | Avonblue, Berkeley, Bluecrop |
| | | 3 | greenish white | Blueray, Collins, Coville |
| | | 4 | light pink | Bluebell, Delite, Dixi, Tifblue |
| 19 | Observation (c) VG | 3 | small | |
| | | 5 | medium | |
| | | 7 | large | |
| 20 | Observation (c) VG | 1 | absent or very weak | |
| | | 3 | weak | |
| | | 5 | medium | |
| | | 7 | strong | |
| 21 | Observaton (c) VG | 1 | absent | Herbert |
| | | 9 | present | Aliceblue Berkeley, Dixi |
| 22 | Observation (d) VG | 3 | sparse | Homebell, Jersey, Woodard |
| | | 5 | medium | Bluechip, Bluecrop, Bluetta |
| | | 7 | dense | Darrow, Herbert, Patriot |
| 23 | Observation VG | 3 | light | |
| | | 5 | medium | |
| | | 7 | dark | |
| 24 | Observation (d) VG | 3 | small | Homebell, June, Northblue |
| | | 5 | medium | Collins, Earliblue |
| | | 7 | large | Berkeley, Bluecrop, Spartan |
| 25 | Observation (d) VG | 1 | elliptic | |
| | | 2 | round | Berkeley, Jersey, Sharpblue |
| | | 3 | oblate | Earliblue, Harison, Woodard |
| 26 | Observation (d) VG | 3 | small | |
| | | 5 | medium | |
| | | 7 | large | |
| 27 | Observation (d) VG | 1 | star | |
| | | 2 | circular | |
| 28 | Observation (d) VG | 1 | erect | |
| | | 2 | erect to semi-erect | |
| | | 3 | semi-erect | |
| | | 4 | level | |
| 29 | Observation (d) VG | 1 | incurving | |
| | | 2 | straight | |
| | | 3 | reflexed | |
| 30 | Observation (d) VG | 3 | small | Avonblue, Bluechip, Sharpblue |
| | | 5 | medium | Blueray, Woodard |

TABLE 1-continued (Comparison of characteristics among varieties)

| | | | | |
|---|---|---|---|---|
| | | 7 | large | Coville, Darrow, Homebell |
| 31 | Observation (d) VG | 3 | shallow | Bluecrop, Rancocas, Tifblue |
| | | 5 | medium | Earliblue, Jersey |
| | | 7 | deep | Blueray, Collins, Dixi |
| 32 | Observation (d) VG | 1 | very weak | |
| | | 3 | weak | Dixi, Herbert, Sharpblue |
| | | 5 | medium | Collins, Coville |
| | | 7 | strong | Avonblue, Bluecrop, Tifblue |
| 33 | Observation (d) VG | 1 | light blue | Berkeley, Bluechip, Tifblue |
| | | 2 | medium blue | Blueray, Jerse, June |
| | | 3 | dark blue | Dixi, Homebell |
| | | 4 | blue red | |
| 34 | Observation (d) VG/VS | 3 | soft | Herbert, Homebell, Spartan |
| | | 5 | medium | Collins, Dixi |
| | | 7 | firm | Coville, Southland |
| | | 9 | very firm | |
| 35 | Observation (d) VG | 1 | white | Berkeley, Bluecrop, Blueray |
| | | 2 | cream | Earliblue |
| | | 3 | light green | Bluechip, Lateblue, Sharpblue |
| | | 4 | light purple | Aliceblue, Delite, Homebell |
| 36 | Observation (d) VG | 3 | low | Avonblue, Bluechip |
| | | 5 | medium | Berkeley, Bluetta, Spartan |
| | | 7 | high | Aliceblue, Bluecrop, Blueray |
| 37 | Observation (d) VG | 3 | low | Earliblue, Homebell |
| | | 5 | medium | Blueray, Herbert |
| | | 7 | high | Collins, Elliott, Lateblue |
| 38 | Observation (c) VG | 1 | on one-year-old shoots only | |
| | | 2 | on one-year-old and current season's shoots | |
| 39 | Observation (d) VG | 3 | less | Earliblue, Herbert, Spartan |
| | | 5 | medium | Avonblue, Berkeley, Bluechip |
| | | 7 | much | Briteblue, Climax, Darrow |
| 40 | Measurement MG | 3 | early | Avonblue, Beckyblue, Sharpblue |
| | | 5 | medium | Darrow, Weymouth |
| | | 7 | late | Elliott, Lateblue |
| 41 | Measurement MG | 1 | very early | |
| | | 3 | early | |
| | | 5 | medium | Bluecrop, Collins, Woodard |

TABLE 1-continued (Comparison of characteristics among varieties)

| | | | | |
|---|---|---|---|---|
| | | 7 | late | Dixi, Herbert, Lateblue |
| | | 9 | very late | |
| 42 | Measurement MG | 3 | early | |
| | | 5 | medium | |
| | | 7 | late | |
| 43 | Measurement MG | 1 | very early | |
| | | 3 | early | Avonblue, Earliblue, Weymouth |
| | | 5 | medium | Herbert, Jersey |
| | | 7 | late | Briteblue, Elliott, Tifblue |
| | | 9 | very late | |
| 44 | Measurement MG | 3 | short | Darrow, Northblue |
| | | 5 | medium | Berkeley, Bluecrop |
| | | 7 | long | Briteblue, Tifblue, Woodard |
| 45 | Measurement MG | 3 | early | |
| | | 5 | medium | |
| | | 7 | late | |

| | The present variety | Control Varieties | |
|---|---|---|---|
| Charact. No | RYOKU NH-13 | Blueray | Chandler |
| 1 | 7 | 6 | 7 |
| 2 | 7 | 5 | 7 |
| 3 | 1 | 1 | 2 |
| 4 | 5 | 5 | 4 |
| 5 | 6 (212 mm) | 5 (173 mm) | 7 (288 mm) |
| 6 | 7 (20.4 mm) | 3 (14.0 mm) | 6 (16.7 mm) |
| 7 | 5 (70.4 mm) | 5 (68.0 mm) | 6 (67.0 mm) |
| 8 | 5 (39.2 mm) | 5 (31.0 mm) | 6 (36.3 mm) |
| 9 | 5 (1.80) | 5 (2.20) | 5 (1.85) |
| 10 | 3 | 3 | 3 |
| 11 | 5 | 5 | 5 |
| 12 | 2 | 2 | 2 |
| 13 | 5 | 5 | 5 |
| 14 | 1 | 1 | 1 |

TABLE 1-continued (Comparison of characteristics among varieties)

| | | | |
|---|---|---|---|
| 15 | 5 | 7 | 6 |
| 16 | 7 (42.0 mm) | 6 (28.7 mm) | 6 (35.1 mm) |
| 17 | 2 | 1-2 | 2-3 |
| 18 | 1 | 3 | 1 |
| 19 | 7 | 5 | 7 |
| 20 | 1 | 3 | 1 |
| 21 | 1 | 9 | 9 |
| 22 | 6 (slightly dense) | 7 | 7 |
| 23 | 4 | 7 | 3 |
| 24 | 7 (3.81 g) | 5 (2.89 g) | 7 (5.72 g) |
| 25 | 3 | 3 | 3 |
| 26 | 6 (2.54 mm) | 7 (3.80 mm) | 7 (3.98 mm) |
| 27 | 2 | 2 | 2 |
| 28 | 2 | 3 | 3 |
| 29 | 3 | 1 | 3 |
| 30 | 7 (7.60 mm) | 6 (4.40 mm) | 7 (6.46 mm) |
| 31 | 7 (3.22 mm) | 7 (2.60 mm) | 7 (2.32 mm) |
| 32 | 5 | 5 | 5 |
| 33 | 2 | 2 | 2 |
| 34 | 5 | 6 | 5 |
| 35 | 3 | 3 | 3 |
| 36 | 7 (Bx 12.3) | 7 (Bx 12.6) | 6 (Bx 13.0) |
| 37 | 7 (pH 2.55) | 5 (pH 3.12) | 6 (pH 2.96) |
| 38 | 1 | 1 | 1 |
| 39 | 3 | 3 | 3 |
| 40 | 5 Apr. 7 (2016) | 5 Apr. 6 (2016) | 5 Apr. 8 (2016) |
| 41 | 6 Apr. 26 (2016) | 5 Apr. 23 (2016) | 6 Apr. 27 (2016) |
| 42 | — | — | — |
| 43 | 6 Middle July to late July | 5 Middle July to late July | 7 Late July to early August |
| 44 | 6 | 5 | 5 |
| 45 | — | — | — |

What is claimed is:

1. A new and distinct variety of *Vaccinium corymbosum* L. plant named 'RYOKU NH-13', as described and illustrated herein.

* * * * *